United States Patent [19]

Bergersen

[11] Patent Number: 4,830,612

[45] Date of Patent: May 16, 1989

[54] DECIDUOUS DENTITION TREATMENT APPLIANCE AND ORTHODONTIC METHOD

[76] Inventor: Earl O. Bergersen, 950 Green Bay Rd., Winnetka, Ill. 60093

[21] Appl. No.: 54,287

[22] Filed: May 26, 1987

[51] Int. Cl.$^4$ ............................................... B61C 3/00
[52] U.S. Cl. ............................................ 433/6; 433/24
[58] Field of Search ........................... 433/6, 215, 24; 128/136

[56] References Cited

U.S. PATENT DOCUMENTS

| | | | |
|---|---|---|---|
| 3,334,417 | 8/1967 | Spengeman | 128/136 |
| 3,939,598 | 2/1976 | Bergersen | 433/6 |
| 4,139,944 | 2/1979 | Bergersen | 433/6 |
| 4,179,811 | 12/1979 | Hinz | 433/6 |

Primary Examiner—John J. Wilson

[57] ABSTRACT

A method and an orthodontic positioner for preventing or correcting overbite and/or overjet at a deciduous dentition stage wherein a patient has only deciduous teeth is provided. A positioner having depressions or slots sized for permanent teeth but receiving deciduous teeth will assist in shaping the jaw to provide early correction of detention problem.

9 Claims, 1 Drawing Sheet

DECIDUOUS DENTITION TREATMENT APPLIANCE AND ORTHODONTIC METHOD

BACKGROUND OF THE INVENTION

1. Field of the Invention

This invention relates to tooth positioning appliances and a method for their use, and in particularly to an appliance and method of use in a very young child.

2. Brief Description of the Prior Art

Orthodontic appliances are used quite widely to correct dentition problems such as overbite and overjet. These appliances include "active" type appliances such as bands and wires or, "passive" type appliances such as the orthodontic positioners described in my prior U.S. Pat. Nos. 3,898,736 and 4,139,944.

In the past, the orthodontic treatment has generally occurred after all permanent teeth have replaced the deciduous teeth or, as is discussed in my second patent cited above, during a mixed dentition stage, that is, after some permanent teeth have erupted, but prior to all permanent teeth erupting.

It was recognized in my second patent discussed above that some problems could be discernable after the eruption of some dentition permanent teeth, yet prior to eruption of all permanent teeth.

It was not recognized, however, that any problems could be recognized or treated prior to the eruption of any permanent teeth, that is when only deciduous teeth are present in the patient's mouth.

SUMMARY OF THE INVENTION

The present invention recognizes that some dentition problems may be avoided by use of an appliance at a very young age when only deciduous teeth are present in the mouth and before any permanent teeth have erupted.

Correction of the overjet before the permanent incisors erupt can prevent the deep overbite from developing and provide a greater amount of effective mandibular growth since the inhibiting effect of the overbite on the forward position of the mandible with condylar growth is removed. The philosophy of the appliance embodying the principles of the present invention is to create an environment for the maximum anterior positioning effect of mandibular growth by removing all interferences early in the growth period of a child prior to the eruption of any permanent teeth. By so doing, the permanent teeth will erupt into a normal environment and develop into a normal dentition while many years of lower jaw growth still remain.

The appliance is designed to fit various sizes of deciduous dentitions from relatively small sized teeth to relatively large sized teeth. There is a slot in the posterior segment to accomodate the upper and lower first and second deciduous molars on both sides. There are individual depressions in the appliance for the upper and lower deciduous canines as well as the lower deciduous central and lateral incisors. The area of the upper deciduous central and lateral incisors is represented by a slot that encompasses all four teeth in one opening. It is not necessary that there is any space created for the first permanent molars.

The appliance is designed antero-posteriorly in an almost end-to-end anterior position so that the child has to bring his or her lower jaw forward to correctly get into the appliance. Vertically there is more material in front than in back to open the bite in the posterior section and discourage the upper and lower incisors from over erupting into a deep anterior vertical overbite. The collagenous fibers then develop and fix the teeth into an ideal overbite relationship as the permanent incisors fully erupt. The appliance is purposefully shortened posteriorly to be no longer than the most distal extent of the lower second deciduous molar. This allows the first permanent molars to erupt into the mouth further than they usually do and enhance the bite opening. If they erupt enough and no further eruption is desired for fear of opening the bite too much, then the next age series appliance is used that will cover the occlusal surfaces of the upper and lower first permanent molars. If the appliance is worn past the six year age, permanent teeth begin to erupt. The jaw relationship should be corrected to within two millimeters of a class I relation anteriorly by the time the lower and upper permanent centrals begin their eruption into the mouth. In this way they will be allowed to erupt further and therefore will be prevented from developing into a deep vertical overbite. The upper and lower lateral incisors will then fall into position into a similar way.

The appliance is to be worn by the very young child (about 2–6 years of age) passively while they are asleep, although day time exercise may be necessary of from one to four hours per day in difficult or resistant cases. If the use of the appliance is started at 2–4 years of age, the use of the appliance can be stopped altogether or worn as a retainer until the first permanent molars start to come in at six years of age and again as the permanent incisors begin erupting about seven years of age. After upper and lower incisors have fully erupted in place, the appliance can be worn as a retainer to hold them in position if there is a tendency toward relapse or discontinued if the teeth appear stable.

The appliance itself is a U-shaped device with different slots or spaces for all of the teeth as individual units or as slots for groups of teeth. There is a slot in the posterior part of the appliance to receive the first and second deciduous molar teeth and usually a slot for the anterior (deciduous teeth and later the permanent) upper incisors. There are usually slots for individual lower teeth, sized and spaced for the permanent lower incisors which will create additional room in cases with closely spaced deciduous incisors. The upper and lower deciduous canines will usually have individual slots. The material used is of a resilient nature.

DESCRIPTION OF THE PREFERRED EMBODIMENTS

Figure 1:
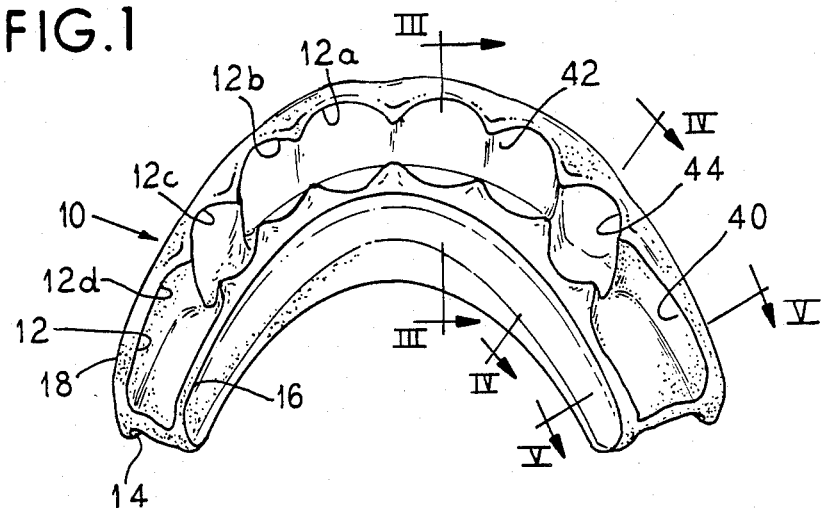
FIG. 1 is a plan view of an orthodontic appliance embodying the principles of the present invention.

A retainer 10 is shown in the figures which is generally U-shaped in plan so as to conform to typical human mouth configuration and is generally H-shaped in cross section providing an upper or superior tooth receiving trough 12 and a lower or inferior tooth receiving trough 14. The sides of the troughs 12 and 14 are bounded by a lingual flange 16 which covers the rear of the teeth of the upper and lower arch and a labial and buccal flange 18 which covers the front of the teeth of both arches.

Both the superior and inferior tooth receiving troughs 12, 14 are provided with a plurality of tooth receiving depressions or slots such as 12a, 12b, 12c and 12d, of different configurations for receiving the different deciduous teeth of the mouth from the central incisors through the first and second deciduous molars.

Figure 3:
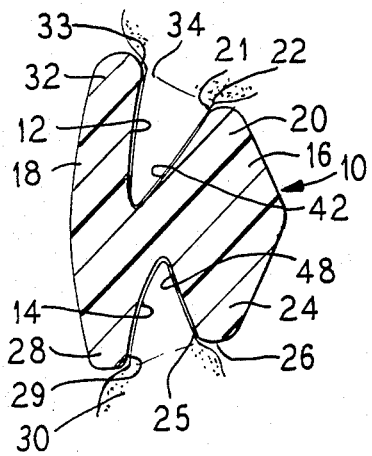
FIG. 3 is a sectional view taken generally along the lines III—III of FIG. 1.
Figure 4:
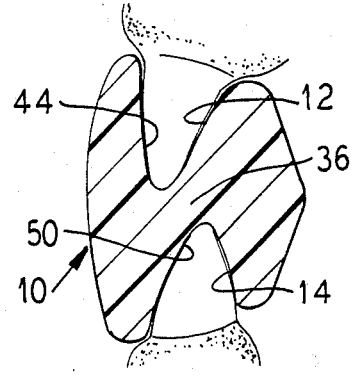
FIG. 4 is a sectional view taken generally along the lines IV—IV of FIG. 1.
Figure 5:
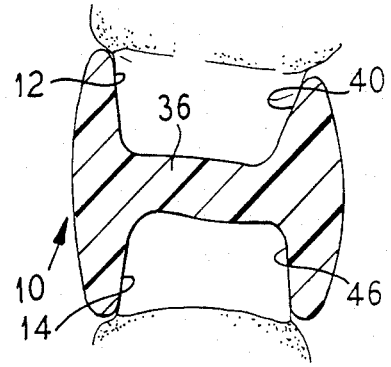
FIG. 5 is a sectional view of the appliance taken generally along the lines V—V of FIG. 1.
Figure 2:
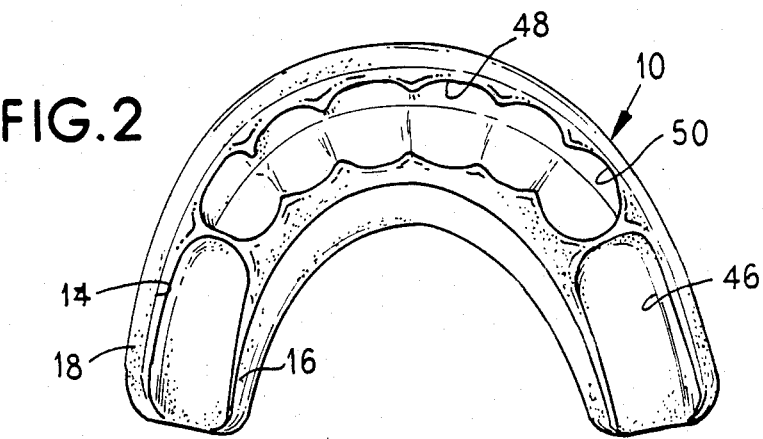
FIG. 2 is a bottom view of the appliance of FIG. 1.

As best seen in FIGS. 3 through 5, an upper portion 20 of the lingual flange 16, which secures the lingual cingulum areas of the upper anterior teeth and lingual surfaces of the lingual cusps of the upper posterior teeth, includes an inwardly directed rib 21 and covers a portion of the upper lingual gingival area 22. A lower portion 24 of the lingual flange 16 generally embraces the cingulum area of the lower anterior teeth and the lingual surface of the lingual cusps of the lower posterior teeth and includes an inwardly directed rib 25. This flange also extends over a portion of the lower lingual gingival tissue 26. A lower portion 28 of the labial and buccal flange 18 which covers the labial and buccal surfaces of the lower anterior and posterior teeth includes an inwardly directed rib 29 and also extends over a portion of the lower labial and buccal gingival tissue 30 and an upper portion 32 of the labial and buccal flange 18 has an inwardly directed rib 33 which covers the entire labial and buccal surfaces of the upper anterior and posterior teeth and also embraces a small portion of the upper gingival tissue 34.

The various pockets (such as 12a and 12b) in the retainer for the upper and lower teeth are to be formed in the retainer sized for the permanent teeth to provide a lateral spread of the jaw to prevent later crowding by the permanent teeth. This can be done more so at a young age (of 2-6 years) since the mouth is more plastic at this age than at a later age when some or all of the permanent teeth have erupted. An isthmus 36 joins the lingual and buccal or labial halves of the positioner and is generally thin, though it differs in vertical dimension or thickness between the posterior region and anterior region by generally providing more material in the front or anterior portion than in the back portion in order to open the bite in the posterior section and to discourage the upper and lower incisors from over erupting into a deep anterior vertical overbite. Thus, the positioner allows the teeth to erupt to a certain point and then halts the eruption at that point while allowing the posterior teeth to erupt to a somewhat greater distance.

The provision of the troughs 12 and 14 requires the child to bring his or her lower jaw forward to correctly get it into the appliance and by pulling the jaw forward causes growth in the child's mouth and jaw to mimic that position to result in a more desireable dentition.

As is true in my prior positioner appliances, it is desireable to make the tooth positioner out of a semi-resilient plastic transparent material. The transparency enables the dental practitioner to actually see where the tooth movement will take place by observing blanching of tissue around the teeth and also enables him to detect potential soft tissue sore spots due to abnormal impingement of the flanges of the tooth positioner.

The positioner 10 is preferred to have a slot 40 in the posterior part of the appliance to receive the first and second deciduous molar teeth and a continuous slot 42 for the interior (deciduous teeth and later the permanent) upper incisors. A separate slot or depression 44 is provided for the upper canines.

The inferior tooth receiving trough 14 includes a slot 46 for the first and second deciduous molar teeth and individual slots or depressions 48 for individual lower teeth which are sized for the permanent lower incisors. These individual slots, sized for the permanent lower incisors, will create additional room in cases with closely spaced deciduous incisors. Also, separate lower canine slots 50 are provided.

The positioner 10 differs from the positioners described in my prior two patents cited above in that the posterior portion of the positioner is made shorter and stops short of the position where the first permanent molar would erupt. Also, the flanges in the posterior region are tapered to a greater degree to provide clearance to the surrounding tissue. Also, the posterior portion is preferable slotted to receive the two deciduous molars as opposed to having individual slots or depressions for receiving individual teeth.

The procedure for use of the appliance of the present invention would be to provide a properly sized appliance to the child who is in the age range of about 2 to 6 years. The appliance would be worn by the child passively while the child is asleep, although daytime exercise may be necessary in difficult or resistant cases of from one to four hours per day. The appliance would be used passively in this manner until the first permanent molars begin to erupt at about 6 years of age at which time the use of the appliance could be stopped altogether or it could be continued to be worn as a retainer. After the upper and lower permanent incisors have fully erupted in place, the appliance could be worn as a retainer to hold them in position if there is a tendency toward relapse. Use of the device could be discontinued if the teeth appear stable.

As is apparent from the foregoing specification, the invention is susceptible of being embodied with various alterations and modifications which may differ particularly from those that have been described in the preceeding specification and description. It should be understood that I wish to embody within the scope of the patent warranted hereon all such modifications as reasonably and properly come within the scope of my contribution to the art.

I claim as my invention:

1. A method of positioning deciduous teeth comprising the steps of:

providing an orthodontic positioner of the type which is generally U-shaped in plan view and includes in at least one of the top or bottom thereof a tooth receiving trough for receiving and positioning teeth, said providing step comprising selecting a preformed positioner having in the trough or troughs therein at least depressions of a size and shape at least as large as deciduous teeth of a patient said depressions having a spacing approximately equal to the desired spacing for permanent teeth of the patient, applying the positioner for use by a patient at a deciduous dentition stage of development, wherein the patient has only deciduous teeth, by applying said selected preformed positioner to the patient's teeth, such use continuing for at least a portion of the time from the initial application of the positioner to the time that first permanent molars start to erupt.

2. The method of claim 1, wherein said providing step includes providing a positioner having tooth receiving troughs in both the top and bottom thereof.

3. The method of claim 1, wherein said applying step comprises applying the positioner for use until the permanent incisors begin erupting.

4. The method of claim 1, wherein said applying step comprises applying the positioner for use until after upper and lower incisors have fully erupted in place.

5. The method of claim 1, wherein said providing step includes selecting a preformed positioner having in the trough or troughs thereof depressions of a size and shape for a person having permanent teeth.

6. An orthodontic positioner of the type which is generally U-shaped in plan view and includes a tooth receiving trough formed between side flanges in at least one of the upper or lower sides thereof, which trough includes tooth receiving depressions for receiving and positioning teeth, said positioner including depressions sized to receive permanent incisors and permanent canines in which are to be received the deciduous incisors and canines, and an extended slot for receiving deciduous molars, a posterior portion of the positioner stopping short of the position where a first permanent molar would erupt and said flanges in the posterior region being tapered to provide clearance to surrounding tissue.

7. An orthodontic positioner according to claim 6, said positioner extending posteriorly to a second deciduous molar.

8. An orthodontic positioner according to claim 6, wherein tooth receiving troughs are provided in both the top and the bottom thereof and an isthmus between said troughs having a vertical thickness greater in a portion of the trough designed to receive the incisors than a portion designed to receive said deciduous molars.

9. An orthodontic positioner according to claim 6, wherein said positioner has tooth receiving troughs in both the top and bottom thereof.

* * * * *